United States Patent [19]

Kleemann et al.

[11] 4,222,956

[45] Sep. 16, 1980

[54] PROCESS FOR THE PRODUCTION OF CYANOCARBOXYLIC ACIDS

[75] Inventors: Axel Kleemann; Peter Schalke; Detlef Arnoldi, all of Hanau, Fed. Rep. of Germany

[73] Assignee: Deutsche Gold- und Silber-Scheideanstalt vormals Roessler, Frankfurt, Fed. Rep. of Germany

[21] Appl. No.: 12,133

[22] Filed: Feb. 14, 1979

[30] Foreign Application Priority Data

Mar. 17, 1978 [DE] Fed. Rep. of Germany ....... 2811702

[51] Int. Cl.³ ................ C07C 120/00; C07C 121/407
[52] U.S. Cl. ............................. 260/465.4; 260/465.6; 260/404
[58] Field of Search ...................................... 260/465.4

[56] References Cited

U.S. PATENT DOCUMENTS

| | | | |
|---|---|---|---|
| 2,338,834 | 1/1944 | Britton et al. | 260/465.4 |
| 2,480,380 | 8/1949 | Nicholl et al. | 260/465.4 |
| 2,985,682 | 9/1961 | Raffelson | 260/465.4 X |
| 3,360,540 | 12/1967 | Sennewald et al. | 260/465.4 X |
| 3,375,268 | 3/1968 | Kesslin et al. | 260/465.4 |
| 3,384,654 | 5/1968 | Sennewald et al. | 260/465.4 X |
| 3,655,723 | 4/1972 | Drinkard, Jr. | 260/465.4 X |
| 3,773,808 | 11/1973 | Wesselman et al. | 260/464 X |
| 3,798,256 | 3/1974 | King et al. | 260/464 X |

FOREIGN PATENT DOCUMENTS 1938080 2/1970 Fed. Rep. of Germany.
824640 12/1959 United Kingdom.

OTHER PUBLICATIONS

MiGrdichian, "The Chemistry of Organic Cyanogen Compounds" (1947), pp. 173-176.

*Primary Examiner*—Joseph Paul Brust
*Attorney, Agent, or Firm*—Cushman, Darby & Cushman

[57] ABSTRACT

Cyanocarboxylic acids are prepared by reacting halocarboxylic acids with cyanohydrins, preferably at a pH of 9 to 11.

18 Claims, No Drawings

PROCESS FOR THE PRODUCTION OF CYANOCARBOXYLIC ACIDS

BACKGROUND OF THE INVENTION

The invention is directed to a process for the production of a cyanocarboxylic acid by reacting a halocarboxylic acid with a substance yielding cyanide ions. The invention is particularly concerned with a process for the production of cyanoacetic acid from chloroacetic acid.

It is known to produce cyanoacetic acid by the action of cyanides and chloroacetic acid. For this purpose the chloroacetic acid in the presence of water is converted by means of sodium carbonate into its sodium salt, this is reacted with sodium cyanide and subsequently the reaction mixture is acidified. The water free cyanoacetic acid is recovered from this mixture which besides water contains inorganic salts by extraction with ketones having 4 to 5 carbon atoms, methyl isobutyl ketone or mesityl oxide (Britton U.S. Pat. No. 2,338,834 and Nicholl, U.S. Pat. No. 2,480,380) or first is freed from water under reduced pressure and then is extracted with aliphatic esters (Lonza, British Pat. No. 824,640). The disadvantage of these processes is that side products are formed which can only be removed with difficulty so that a cyanoacetic acid obtained by these processes contains undesired impurities and is colored.

It is also known to carry out the reaction in the presence of alkanols such as n-butanol (German OS No. 1930080). This process chiefly serves for the production of the corresponding ester of cyanoacetic acid.

SUMMARY OF THE INVENTION

There has now been found a process for the production of cyanocarboxylic acids, e.g. cyanoalkanoic acids by reaction of halocarboxylic acids, e.g. haloalkanoic acids, with a compound yielding cyanide ions which is characterized by the reaction being carried out with a cyanohydrin. In this process the cyanocarboxylic acids are produced with very good yields in high purity. Although the process is particularly suited for the conversion of chloroacetic acid to cyanoacetic acid, it is generally usable for the production of cyanocarboxylic acids from aliphatic mono halogenated carboxylic acids.

As starting materials there are employed unbranched or branched aliphatic mono halogenated carboxylic acids, especially those which are halogenated in the $\alpha$ or $\omega$-position. As halogens there can be used iodine or more preferably bromine or most preferably chlorine. Suitable acids besides chloroacetic acid are for example bromoacetic acid, 2-bromopropionic acid, 3-chloropropionic acid, 4-chlorobutyric acid and 2-chlorocaproic acid, i.e., haloalkanoic acids having 2 to 6 carbon atoms. Additional haloalkanoic acids include iodoacetic acid, 3-methyl-4-chlorobutyric acid, 18-chlorostearic acid, 10-chlorodecanoic acid, e.g., haloalkanoic acids containing 2 to 18 carbon atoms.

According to the invention the conversion of the halocarboxylic acid takes place by means of cyanohydrins of the general formula

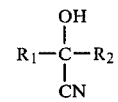

in which $R_1$ is hydrogen or an unbranched or branched alkyl group, preferably with 1 to 8 carbon atoms, and especially with 1 to 4 carbon atoms and $R_2$ is the same or different unbranched or branched alkyl group, preferably with 1 to 8 carbon atoms, and especially with 1 to 4 carbon atoms. Examples of such cyanohydrins are acetone cyanohydrin, acetaldehyde cyanohydrin, methyl ethyl cyanohydrin, methyl propyl cyanohydrin, methyl isopropyl cyanohydrin, methyl butyl cyanohydrin, methyl sec. butyl cyanohydrin, diethyl cyanohydrin, dibutyl cyanohydrin, ethyl propyl cyanohydrin, dipropyl cyanohydrin, methyl octyl cyanohydrin, dioctyl cyanohydrin, methyl amyl cyanohydrin, di sec. butyl cyanohydrin, and methyl isobutyl cyanohydrin. In the reaction the corresponding oxo compounds are formed from the cyanohydrins.

The reaction is carried out in the presence of alkaline acting materials. For this purpose it is suitable to use compounds which form salts that are readily soluble in water with the halocarboxylic acids and the cyanide ions. For example there can be used ammonia, amines such as triethylamine or trimethylamine, metal oxides, or metal hydroxides such as alkaline earth or alkali metal hydroxides, e.g., calcium hydroxide, sodium hydroxide or potassium hydroxide. Sodium and potassium hydroxide are preferred.

To carry out the process of the invention the salts of the halocarboxylic acids, especially their alkali metal salts are added. In case as starting material there is used the halocarboxylic acid itself, it is converted into the salt before the reaction with the cyanohydrin. However, there can also be reacted directly the halocarboxylic acid with the cyanohydrin in the presence of alkaline acting material.

The reaction conditions such as temperature and pressure and molar ratios are interdependent and are adjusted in a given case according to the type of materials employed.

Generally the reaction is carried out at temperatures between about 40° and 130° C., preferably at temperatures between 70° and 90° C. It is advantageous in many cases to work at the boiling temperature of the mixture. Although the pressure can be selected at random, thus at normal pressure as well as at lower or higher pressure, it is generally suitable not to deviate substantially from normal pressure. In a given case the pressure is adjusted according to the volatility of the materials at the temperatures concerned.

The molar ratios of halocarboxylic acid to cyanohydrin can be chosen within wide ranges, both stoichiometric and also over or under stoichiometric. However, in general it is suitable per mole of halocarboxylic acid to use at least about 1 mole of cyanohydrin. Preferably there are used 1.01 to 1.30 moles, especially 1.05 to 1.15 moles, of cyanohydrin per mole of halocarboxylic acid.

The reaction takes place in the presence of water. In most cases it it suitable to use the least possible amount of water, however, with advantage sufficient water is added that the halocarboxylic acid in the form of its salt is present completely dissolved.

There is needed the alkaline acting material in an amount equivalent to the cyanohydrin. In case the halocarboxylic acid is not added in the form of salt it is necessary to add additionally an amount of alkaline acting material equivalent to this acid. Generally it is suitable to use the alkaline acting material in at least equivalent amount. Preferably there is used an excess of 0.01 to 0.20, particularly of 0.05 to 0.10 equivalent.

It is advantageous to inject the alkaline acting material into the reaction mixture in such manner that this is continuously weakly alkaline. The pH is adjusted to a certain extent according to the type of acid and the type of alkaline acting material. Generally it amounts to about 8 to 12. In most cases a pH between 9 and 11 is advantageous. For example in the case of the conversion of chloroacetic acid in the presence of alkali metal hydroxide there is preferred a pH between 9.5 and 11.0, particularly between 9.8 and 10.5.

In most cases, particularly if a cyanohydrin is used, from which an oxo compound is formed, which is miscible with water in a wide range or is completely miscible, as for example, acetone cyanohydrin, it is suitable to expel the oxo compound during the reaction.

After the reaction there are present in the reaction mixture the cyanocarboxylic acid as the salt as well as foreign salts. To recover the cyanocarboxylic acid it is general suitable to acidify the reaction mixture. Preferably for this purpose there serve strong mineral acids such as sulfuric acid, hydrochloric acid or hydrobromic acid. The cyanocarboxylic acid is then separated from the mixture, suitably by an extraction with a ketone. There are particularly suitable as extraction agents methyl ethyl ketone, diethyl ketone, methyl isopropyl ketone and methyl isobutyl ketone.

The process of the invention is carried out in a particularly advantageous form if there is added from these ketones the one corresponding to the cyanohydrin. In such cases the ketone formed from the cyanohydrine can serve as the extraction agent.

Generally the cyanocarboxylic acids result in such pure form in the extraction that they can be used directly for further use, the cyanoacetic acid for example for use in the production of esters of cyanoacetic acid and esters of malonic acid.

Unless otherwise indicated all parts and percentages are by weight.

The process can comprise, consist essentially of or consist of the steps set forth and the materials can comprise, consist essentially of or consists of those set forth.

EXAMPLE 1

150 grams (1.3 moles) of the sodium salt of chloroacetic acid were dissolved in 300 ml of water. The solution was adjusted to a pH of 8 with a 40 percent aqueous sodium hydroxide solution. Then there were added 116 grams (1.4 moles) of acetone cyanohydrin and the mixture was heated to 60° C. Additionally there were gradually added 135 grams of the 40 percent sodium hydroxide solution in such manner that the pH of the mixture continuously remained between 9.5 and 10.5. During the addition of the sodium hydroxide solution the mixture warmed up so that it boiled, temperature between 70° and 80° C., and acetone distilled off. The mixture was held at the boiling temperature until no more acetone passed over, subsequently held a further hour at 80° C. and cooled to 20° C. Then the mixture was adjusted to pH 1 with 110 ml of 12.5 N aqueous hydrochloric acid and extracted in a column with 1200 ml of methyl ethyl ketone. The ketone was expelled from the extract under reduced pressure. There remained 105 grams of residue. This solidified in crystalline form. It consisted of 98% cyanoacetic acid. This corresponds to a yield of cyanoacetic acid of 94% based on the chloroacetic acid added.

EXAMPLE 2

The procedure was as in Example 1 but there were added 139 grams (1.4 moles) of methyl ethyl cyanohydrin in place of the acetone cyanohydrin. There were obtained 105 grams of 95 percent cyanoacetic acid. The yield of cyanoacetic acid accordingly was 91%.

EXAMPLE 3

The procedure was as in Example 1 but there were only used 150 ml of water and in place of acetone cyanohydrin there were added 160 grams of methyl isopropyl cyanohydrin. For the extraction of cyanoacetic acid from the reaction mixture there was used the distilled methyl isopropyl ketone. There were obtained 104 grams of 98% cyanoacetic acid. The yield of cyanoacetic acid accordingly was 93%.

EXAMPLE 4

The procedure was as in Example 1 but instead of the sodium salt of chloroacetic acid there were added 228 grams (1.3 moles) of the sodium salt of 2-bromopropionic acid. There were obtained 124 grams of 98% 2-cyanopropionic acid. The yield of 2-cyanopropionic acid based on the 2-bromopropionic acid, accordingly was 94%.

EXAMPLE 5

The procedure was as in Example 1 but instead of the sodium salt of chloroacetic acid there were added 190 grams (1.3 moles) of the potassium salt of 3-chloropropionic acid. Instead of the sodium hydroxide solution there was used the corresponding amount of potassium hydroxide. There were obtained 110 grams of 92% 3-cyanopropionic acid. The yield of 3-cyanopropionic acid accordingly was 78%.

What is claimed is:

1. A process for the production of a cyanoalkanoic acid comprising reacting a haloalkanoic acid in the presence of an alkaline acting material with a cyanohydrin of the formula

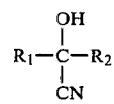

where $R_1$ is hydrogen or alkyl of 1 to 8 carbon atoms and $R_2$ is alkyl of 1 to 8 carbon atoms in the presence of water.

2. A process according to claim 1 wherein $R_1$ is alkyl of 1 to 4 carbon atoms and $R_2$ is alkyl of 1 to 4 carbon.

3. A process according to claim 2 wherein the haloalkanoic acid has 2 to 6 carbon atoms and the cyanoalkanoic acid has 2 to 6 carbon atoms.

4. A process according to claim 3 wherein the halogen of the haloalkanoic is chlorine, bromine, or iodine.

5. A process according to claim 4 wherein the haloalkanoic acid is haloacetic acid and the cyanohydrin is acetone.

6. A process according to claim 5 wherein the haloacetic acid is chloroacetic acid.

7. A process according to claim 1 wherein the pH of the reaction mixture is 9 to 11.

8. A process according to claim 1 wherein the reaction is carried out at a temperature between 40° and 130° C.

9. A process according to claim 8 wherein there is employed at least about 1 mole of cyanohydrin per mole of haloalkanoic acid.

10. A process according to claim 9 wherein there is employed 1.01 to 1.30 moles of cyanohydrin per mole of haloalkanoic acid.

11. A process according to claim 10 wherein there is employed 1.05 to 1.15 moles of cyanohydrin per mole of haloalkanoic acid.

12. A process according to claim 11 wherein the temperature is between 70° and 90° C.

13. A process according to claim 1 wherein there is employed at least about 1 mole of cyanohydrin per mole of salt of haloalkanoic acid.

14. A process according to claim 13 wherein there is employed 1.01 to 1.30 moles of cyanohydrin per mole of haloalkanoic acid.

15. A process according to claim 1 wherein there is employed a salt of the alkanoic acid at a weakly alkaline pH.

16. A process according to claim 15 wherein the pH is 8 to 12.

17. A process according to claim 16 wherein the temperature is 40° to 130° C. and there are employed 1.01 to 1.30 moles of cyanohydrin per mole of salt of haloalkanoic acid.

18. A process according to claim 1 wherein water is the sole solvent added.

* * * * *